United States Patent [19]

Barrett et al.

[11] 4,309,313

[45] Jan. 5, 1982

[54] SYNTHESIS OF CESIUM-CONTAINING ZEOLITE, CSZ-1

[75] Inventors: Michael G. Barrett, Laurel, Md.; David E. W. Vaughan, Flemington, N.J.

[73] Assignee: W. R. Grace & Co., New York, N.Y.

[21] Appl. No.: 152,642

[22] Filed: May 23, 1980

[51] Int. Cl.$^3$ .................. B01J 29/08; B01J 29/28; C01B 33/28

[52] U.S. Cl. .................. 252/455 Z; 423/328; 423/329

[58] Field of Search .................. 423/328–330; 252/455 Z

[56] References Cited

U.S. PATENT DOCUMENTS 3,411,874 11/1968 Ciric .................. 423/328
3,415,736 12/1968 Ciric .................. 423/328
3,904,738 9/1975 Robson .................. 423/328

OTHER PUBLICATIONS

Kokotailo et al., "Molecular Sieve Zeolites-I", ACS, 1971, pp. 109–121.
Barrer et al., "J. Chem. Soc.", (Dalton) 1977, pp. 1020–1026.

*Primary Examiner*—Edward J. Meros
*Attorney, Agent, or Firm*—Edward J. Cabic

[57] ABSTRACT

A new zeolite structure, CSZ-1, has a composition 0.05 to 0.55 $M_2O$:0.45 to 0.95 $Na_2O$:$Al_2O_3$: 3 to 7 $SiO_2$:x $H_2O$ where M is cesium and/or thallium and x is 0 to 10. The zeolite has utility in sorption, separation and catalytic applications. It is made by reacting together sources of silica, alumina, soda, cesia and/or thallia, together with a nucleating agent or solution, followed by hot aging at a temperature between 50° and 160° C.

25 Claims, No Drawings

SYNTHESIS OF CESIUM-CONTAINING ZEOLITE, CSZ-1

BACKGROUND OF THE INVENTION

1. Field of the Invention

This invention relates to a new large pore crystalline aluminosilicate zeolite containing cesium and/or thallium that can be used for sorption, separation and catalyst applications.

2. Description of the Prior Art

Early zeolite synthesis with cesium, Cs, was reported by Barrer and McCallum in 1953 in *J. Chem. Soc.* (London) page 4029, and subsequent work has been reviewed by Barrer and Sieber in 1977 *J. Chem. Soc.* (Dalton) page 1020, in which they synthesized in Cs-Li-$(CH_3)_4N$ systems the wide pore zeolites offretite, ZK-5 previously reported by G. T. Kerr in *Inorg. Chem.* 5, page 1539 (1966), and ZSM-2 previously reported by J. Ciric in U.S. Pat. No. 3,411,874 (1968). Robson, in U.S. Pat. No. 3,904,738 (1975), has also reported the synthesis of a wide pore zeolite Rho in the Na-Cs synthesis system.

3. Object of the Invention

It is an object of this invention to obtain a cesium and/or thallium containing zeolite with a unique x-ray diffraction pattern.

It is a further object of this invention to obtain a large pore cesium and/or thallium containing zeolite with wide pores of about seven Angstrom units and having a high internal pore volume of up to 800 m²/g measured by nitrogen.

It is still a further object of the invention to obtain a cesium and/or thallium containing zeolite which can be used for sorption, separation and catalyst application.

These and further objects will become apparent as the description of the invention proceeds.

SUMMARY OF THE INVENTION

A new zeolite structure, to be named CSZ-1, having a composition 0.05 to 0.55 cesium and/or thallium (Cs, Tl)$_2$O: 0.45 to 0.95 Na$_2$O:Al$_2$O$_3$: 3 to 7 SiO$_2$:x H$_2$O where x is 0 to 10, can be made by reacting together sources of silica, alumina, soda, cesia and/or thallia, together with a nucleating agent or solution, followed by hot aging at a temperature between 50° and 160° C. This material has a new, but indeterminate structure, and novel sorption and catalytic properties. Unlike the previous preparation of the above zeolites, CSZ-1 requires the presence of a nucleant to promote its formation. The CSZ-1 product has high internal pore volume (up to 800 m²/g N$_2$) and wide pores, as shown by sorption of large aromatic molecules. The material has utility in sorption, separation and catalytic applications.

The method of preparing the zeolite comprises forming a mixture containing sources of cesia and/or thallia, an oxide of sodium, an oxide of silicon, an oxide of aluminum, water and sodium aluminosilicate nucleating seeds. The mixture has a final composition in terms of mole ratios of oxides and metal atoms within the following ranges M/(M+Na): 0.02–0.3
Na$_2$O/SiO$_2$: 0.15–0.60
SiO$_2$/Al$_2$O$_3$: 6–30
H$_2$O/SiO$_2$: 8–50 where M is Cs or Tl. The seeds are present in an amount which yields 0.1 to 25 mole percent of the total final alumina content. Next this composition is mixed to obtain a homogeneous reaction mixture which forms a gel, and then the resulting gel is heated at a temperature of at least 50° C. until the crystals of the zeolite are formed.

More preferred compositions utilize a starting mixture having a final composition in the following ranges Cs/(Cs+Na): 0.02–0.15
Na$_2$O/SiO$_2$: 0.15–0.60
SiO$_2$/Al$_2$O$_3$: 6–20
H$_2$O/SiO$_2$: 15–30.

The cesia or thallia can be added either as a separate salt or in the seed composition. In addition the cesium can be obtained by acid leaching of a cesium containing mineral such as pollucite.

DESCRIPTION OF THE SPECIFIC EMBODIMENTS

CSZ-1 is identified primarily by its unique x-ray diffraction pattern (Table I), chemical composition, and general properties.

TABLE I

X-Ray Diffraction Patterns for CSZ-1

| Na-Cs-CSZ-1 | | | Na-Tl-CSZ-1 | | |
|---|---|---|---|---|---|
| dÅ | 2θ | I/Io | dÅ | 2θ | I/Io |
| 15.14 | 5.83 | 30 | 15.09 | 5.85 | 60 |
| 14.24 | 6.20 | 90 | 14.13 | 6.25 | 100 |
| 13.06 | 6.76 | 10 | — | — | — |
| 8.66 | 10.20 | 15 | 8.79 | 10.05 | 10 |
| — | — | — | 7.59 | 11.65 | 12 |
| 7.37 | 12.00 | 10 | 7.43 | 11.90 | 15 |
| 5.61 | 15.77 | 8 | 5.68 | 15.60 | 8 |
| 4.99 | 17.77 | 6 | — | — | — |
| 4.71 | 18.82 | 21 | 4.75 | 18.65 | 15 |
| 4.34 | 20.44 | 8 | 4.37 | 20.30 | 8 |
| — | — | — | 4.27 | 20.80 | 4 |
| 4.14 | 21.45 | 15 | 4.17 | 21.30 | 8 |
| 4.08 | 21.77 | 31 | 4.09 | 21.72 | 20 |
| — | — | — | 3.855 | 23.05 | 3 |
| 3.682 | 24.15 | 65 | 3.699 | 24.04 | 55 |
| 3.521 | 25.27 | 8 | 3.459 | 25.73 | 18 |
| 3.397 | 26.21 | 100 | 3.423 | 26.01 | 24 |
| — | — | — | 3.407 | 26.13 | 8 |
| — | — | — | 3.416 | 26.60 | 8 |
| 3.354 | 26.55 | 20 | 3.323 | 26.81 | 10 |
| 3.331 | 26.74 | 8 | 3.300 | 27.00 | 11 |
| 3.279 | 27.17 | 36 | 3.213 | 27.74 | 20 |
| 3.166 | 28.16 | 5 | 3.175 | 28.08 | 50 |
| — | — | — | 3.108 | 28.70 | 3 |
| 2.997 | 29.79 | 70 | 3.015 | 29.60 | 55 |
| 2.966 | 30.10 | 15 | 2.976 | 30.00 | 12 |
| — | — | — | 2.937 | 30.41 | 10 |
| 2.885 | 30.97 | 40 | 2.854 | 31.32 | 15 |
| — | — | — | 2.831 | 31.58 | 7 |
| — | — | — | 2.802 | 31.91 | 3 |
| 2.780 | 32.17 | 25 | 2.772 | 32.27 | 3 |
| — | — | — | 2.710 | 33.02 | 18 |
| 2.682 | 33.38 | 23 | 2.688 | 33.30 | 17 |
| 2.614 | 34.28 | 7 | 2.627 | 34.10 | 8 |
| 2.547 | 35.20 | 9 | 2.544 | 35.25 | 6 |
| 2.503 | 35.85 | 10 | 2.522 | 35.57 | 19 |
| 2.463 | 36.45 | 18 | 2.483 | 36.15 | 15 |
| 2.369 | 37.95 | 12 | | | |
| 2.347 | 38.31 | 8 | | | |
| 2.302 | 39.10 | 5 | | | |
| 2.276 | 39.56 | 4 | | | |
| 2.168 | 41.62 | 10 | | | |
| 2.062 | 43.82 | 8 | | | |
| 2.026 | 44.68 | 15 | | | |
| 2.018 | 44.88 | 21 | | | |

The x-ray data given in Table I corresponds to a hexagonal unit cell in space group P 6$_3$/mmc with parameters a$_o$=17.4 Angstrom units and c$_o$=28.4 Angstrom units. Sorption and catalytic data indicate an open structure, probably consisting of 12 ring pore openings.

Using the above parameters for a hexagonal unit cell in that space group, a computer generated theoretical x-ray diffraction pattern was obtained for comparison. The calculated pattern is given in Table IA below, and it shows significant agreement. In this regard, the theoretical pattern includes many more lines than are actually detected by the commercial x-ray equipment. In addition some of the lines that are close together may appear as a single larger peak on the x-ray data.

TABLE IA

Theoretical X-Ray Diffraction Pattern for Proposed CSZ-1

Powder lines for a prescribed hexagonal lattice
The space group is P 6₃/mmc

| Direct Cell Parameters | | Reciprocal Cells |
|---|---|---|
| $a_o$ | 17.40 | 0.0664 |
| $b_o$ | 17.40 | 0.0664 |
| $c_o$ | 28.40 | 0.0352 |
| ALPHA | 90.0 | 90.0 |
| BETA | 90.0 | 90.0 |
| GAMMA | 120.0 | 60.0 |

The Wavelength of X-Rays used is 1.5405 Angstroms.

| H | K | L | D | H | K | L | D |
|---|---|---|---|---|---|---|---|
| 1 | 0 | 0 | 15.0688 | 2 | 0 | 1 | 7.2825 |
| 0 | 0 | 2 | 14.2000 | 0 | 0 | 4 | 7.1000 |
| 1 | 0 | 1 | 13.3112 | 2 | 0 | 2 | 6.6556 |
| 1 | 0 | 2 | 10.3344 | 1 | 0 | 4 | 6.4228 |
| 1 | 1 | 0 | 8.7000 | 2 | 0 | 3 | 5.8952 |
| 1 | 0 | 3 | 8.0161 | 2 | 1 | 0 | 5.6955 |
| 2 | 0 | 0 | 7.5344 | 2 | 1 | 1 | 5.5843 |
| 1 | 1 | 2 | 7.4184 | 1 | 1 | 4 | 5.5007 |
| 1 | 0 | 5 | 5.3150 | 4 | 0 | 3 | 3.5002 |
| 2 | 1 | 2 | 5.2861 | 3 | 2 | 0 | 3.4570 |
| 2 | 0 | 4 | 5.1672 | 1 | 0 | 8 | 3.4554 |
| 3 | 0 | 0 | 5.0229 | 3 | 0 | 6 | 3.4448 |
| 3 | 0 | 1 | 4.9462 | 3 | 2 | 1 | 3.4317 |
| 2 | 1 | 3 | 4.8803 | 3 | 1 | 5 | 3.3663 |
| 3 | 0 | 2 | 4.7354 | 3 | 2 | 2 | 3.3589 |
| 0 | 0 | 6 | 4.7333 | 4 | 0 | 4 | 3.3278 |
| 2 | 0 | 5 | 4.5356 | 2 | 1 | 7 | 3.3045 |
| 1 | 0 | 6 | 4.5158 | 4 | 1 | 0 | 3.2883 |
| 2 | 1 | 4 | 4.4427 | 1 | 1 | 8 | 3.2869 |
| 3 | 0 | 3 | 4.4370 | 4 | 1 | 1 | 3.2665 |
| 2 | 2 | 0 | 4.3500 | 3 | 2 | 3 | 3.2473 |
| 3 | 1 | 0 | 4.1793 | 2 | 0 | 8 | 3.2114 |
| 2 | 2 | 2 | 4.1592 | 4 | 1 | 2 | 3.2035 |
| 1 | 1 | 6 | 4.1578 | 2 | 2 | 6 | 3.2029 |
| 3 | 1 | 1 | 4.1348 | 3 | 0 | 7 | 3.1562 |
| 3 | 0 | 4 | 4.1005 | 4 | 0 | 5 | 3.1395 |
| 2 | 1 | 5 | 4.0218 | 3 | 1 | 6 | 3.1329 |
| 3 | 1 | 2 | 4.0093 | 3 | 2 | 4 | 3.1082 |
| 2 | 0 | 6 | 4.0080 | 4 | 1 | 3 | 3.1062 |
| 1 | 0 | 7 | 3.9176 | 1 | 0 | 9 | 3.0886 |
| 3 | 1 | 3 | 3.8233 | 5 | 0 | 0 | 3.0138 |
| 4 | 0 | 0 | 3.7672 | 2 | 1 | 8 | 3.0127 |
| 3 | 0 | 5 | 3.7627 | 5 | 0 | 1 | 2.9969 |
| 4 | 0 | 1 | 3.7345 | 4 | 1 | 4 | 2.9838 |
| 2 | 2 | 4 | 3.7092 | 3 | 2 | 5 | 2.9531 |
| 4 | 0 | 2 | 3.6412 | 5 | 0 | 2 | 2.9481 |
| 2 | 1 | 6 | 3.6403 | 4 | 0 | 6 | 2.9476 |
| 3 | 1 | 4 | 3.6017 | 3 | 1 | 7 | 2.9111 |
| 2 | 0 | 7 | 3.57222 | 2 | 0 | 9 | 2.9106 |
| 0 | 0 | 8 | 3.5500 | 3 | 3 | 0 | 2.9000 |
| 3 | 0 | 8 | 2.8990 | 2 | 1 | 10 | 2.5416 |
| 5 | 0 | 3 | 2.8718 | 5 | 1 | 4 | 2.5289 |
| 4 | 2 | 0 | 2.8477 | 3 | 1 | 9 | 2.5183 |
| 4 | 1 | 5 | 2.8458 | 6 | 0 | 0 | 2.5115 |
| 3 | 3 | 2 | 2.8414 | 6 | 0 | 1 | 2.5017 |
| 0 | 0 | 10 | 2.8400 | 4 | 3 | 0 | 2.4773 |
| 4 | 2 | 1 | 2.8335 | 3 | 2 | 8 | 2.4767 |
| 4 | 2 | 2 | 2.7921 | 6 | 0 | 2 | 2.4731 |
| 3 | 2 | 6 | 2.7917 | 3 | 3 | 6 | 2.4728 |
| 1 | 0 | 10 | 2.7909 | 3 | 0 | 10 | 2.4722 |
| 5 | 0 | 4 | 2.7742 | 4 | 3 | 1 | 2.4679 |

-continued

| H | K | L | D | H | K | L | D |
|---|---|---|---|---|---|---|---|
| 4 | 0 | 7 | 2.7606 | 5 | 1 | 5 | 2.4433 |
| 2 | 1 | 9 | 2.7602 | 2 | 0 | 11 | 2.4424 |
| 2 | 2 | 8 | 2.7504 | 4 | 3 | 2 | 2.4404 |
| 4 | 2 | 3 | 2.7270 | 4 | 2 | 6 | 2.4402 |
| 5 | 1 | 0 | 2.7064 | 6 | 0 | 3 | 2.4275 |
| 3 | 1 | 8 | 2.7057 | 5 | 0 | 7 | 2.4193 |
| 4 | 1 | 6 | 2.7006 | 4 | 0 | 9 | 2.4190 |
| 1 | 1 | 10 | 2.6998 | 5 | 2 | 0 | 2.4129 |
| 5 | 1 | 1 | 2.6942 | 4 | 1 | 8 | 2.4124 |
| 3 | 3 | 4 | 2.6847 | 5 | 2 | 1 | 2.4043 |
| 3 | 0 | 9 | 2.6720 | 4 | 3 | 3 | 2.3966 |
| 5 | 0 | 5 | 2.6622 | 5 | 2 | 2 | 2.3788 |
| 5 | 1 | 2 | 2.6586 | 2 | 2 | 10 | 2.3781 |
| 2 | 0 | 10 | 2.6575 | 6 | 0 | 4 | 2.3677 |
| 4 | 2 | 4 | 2.6431 | 0 | 0 | 12 | 2.3667 |
| 3 | 2 | 7 | 2.6313 | 2 | 1 | 11 | 2.3515 |
| 5 | 1 | 3 | 2.6022 | 5 | 1 | 6 | 2.3495 |
| 4 | 0 | 8 | 2.5836 | 3 | 1 | 10 | 2.3490 |
| 4 | 1 | 7 | 2.5546 | 4 | 3 | 4 | 2.3390 |
| 4 | 2 | 5 | 2.5457 | 5 | 2 | 3 | 2.3382 |
| 1 | 0 | 11 | 2.5447 | 1 | 0 | 12 | 2.3380 |
| 5 | 0 | 6 | 2.5422 | 4 | 2 | 7 | 2.3309 |
| 3 | 2 | 9 | 2.3306 | 5 | 3 | 1 | 2.1465 |
| 6 | 1 | 0 | 2.2980 | 7 | 0 | 1 | 2.1465 |
| 5 | 0 | 8 | 2.2975 | 3 | 0 | 12 | 2.1409 |
| 6 | 0 | 5 | 2.2970 | 6 | 0 | 7 | 2.1354 |
| 3 | 0 | 11 | 2.2962 | 6 | 1 | 5 | 2.1302 |
| 6 | 1 | 1 | 2.2905 | 4 | 0 | 11 | 2.1297 |
| 5 | 2 | 4 | 2.2846 | 5 | 3 | 2 | 2.1284 |
| 1 | 1 | 12 | 2.2837 | 7 | 0 | 2 | 2.1284 |
| 4 | 1 | 9 | 2.1768 | 4 | 3 | 7 | 2.1143 |
| 4 | 3 | 5 | 2.2707 | 4 | 2 | 9 | 2.1141 |
| 6 | 1 | 2 | 2.2685 | 5 | 3 | 3 | 2.0991 |
| 4 | 0 | 10 | 2.2678 | 7 | 0 | 3 | 2.0991 |
| 2 | 0 | 12 | 2.2579 | 2 | 0 | 13 | 2.0982 |
| 5 | 1 | 7 | 2.2515 | 6 | 2 | 0 | 2.0897 |
| 3 | 3 | 8 | 2.2459 | 6 | 2 | 1 | 2.0840 |
| 6 | 1 | 3 | 2.2331 | 4 | 4 | 4 | 2.0796 |
| 4 | 2 | 8 | 2.2213 | 2 | 2 | 12 | 2.0789 |
| 5 | 2 | 5 | 2.2209 | 5 | 2 | 7 | 2.0739 |
| 6 | 0 | 6 | 2.2185 | 3 | 2 | 11 | 2.0686 |
| 3 | 1 | 11 | 2.1965 | 6 | 2 | 2 | 2.0674 |
| 4 | 3 | 6 | 2.1949 | 6 | 1 | 6 | 2.0672 |
| 3 | 2 | 10 | 2.1944 | 5 | 0 | 10 | 2.0669 |
| 6 | 1 | 4 | 2.1863 | 5 | 3 | 4 | 2.0601 |
| 2 | 1 | 12 | 2.1855 | 7 | 0 | 4 | 2.0601 |
| 5 | 0 | 9 | 2.1795 | 3 | 1 | 12 | 2.0594 |
| 4 | 4 | 0 | 2.1750 | 5 | 1 | 9 | 2.0543 |
| 1 | 0 | 13 | 2.1620 | 6 | 0 | 8 | 2.0503 |
| 5 | 3 | 0 | 2.1527 | 6 | 2 | 3 | 2.0405 |
| 7 | 0 | 0 | 2.1527 | 2 | 1 | 13 | 2.0397 |
| 5 | 1 | 8 | 2.1523 | 4 | 3 | 8 | 2.0316 |
| 4 | 4 | 2 | 2.1499 | 4 | 1 | 11 | 2.0307 |
| 5 | 2 | 6 | 2.1495 | 3 | 3 | 10 | 2.0291 |
| 4 | 1 | 10 | 2.1493 | 0 | 0 | 14 | 2.0286 |
| 5 | 3 | 5 | 2.0130 | 6 | 2 | 4 | 2.0046 |
| 7 | 0 | 5 | 2.0130 | 4 | 0 | 12 | 2.0040 |
| 4 | 2 | 10 | 2.0109 | 3 | 0 | 13 | 2.0033 |
| 1 | 0 | 14 | 2.0104 | | | | |

The final synthesis ranges suitable for preparing CSZ-1 are

| Molar Ratios | Typical Ranges | Preferred Ranges |
|---|---|---|
| Cs/(Cs + Na) | 0.02–.3 | 0.02–0.15 |
| Na₂O/SiO₂ | 0.15–0.60 | .2–.4 |
| SiO₂/Al₂O₃ | 6–30 | 7–16 |
| H₂O/SiO₂ | 8–50 | 15–30 |

Seeding or nucleating is a necessary prerequisite for the formation of this new zeolite. Seed compositions having approximate compositions in the range: 4–30 $Na_2O$:1 to 9 $Al_2O_3$: 3–30 $SiO_2$: 250 to 2000 $H_2O$ may be used for the purposes of this invention. The zeolite forming aluminosilicate seeds, sometimes referred to as zeolite nucleation centers, comprise a reaction mixture of soda, silica, alumina and water in the amounts indicated above. To prepare the slurry of zeolite nucleation centers, appropriate amounts of sodium silicate, sodium aluminate and water are combined and aged for a period of about 1 to 500 hours at a temperature of 0° C. to 90° C. with the shorter time required at higher temperatures.

Preparation of suitable zeolite-forming alumina silicate seeds or nucleation centers is disclosed in U.S. Pat. Nos. 3,639,099 to Elliott et al, 3,808,326 to McDaniel et al and 4,178,352 to Vaughan et al, the disclosure of these three being incorporated herein by reference.

Preferred seed compositions have an approximate composition in the range: 16 $Na_2O$:1 to 9 $Al_2O_3$: 15 $SiO_2$: 250 to 2000 $H_2O$.

The seeds or nucleation centers are totally consumed in the production of the final zeolites since it is around these particles that the zeolites grow. The amount of seeds to be added is expressed on the basis of the alumina content and it is expressed as a percentage of the total molar alumina content in the final zeolite product produced. Thus in an example where 6 molar percent seeds are added, this means these seeds will be contributing 6% of the total molar amount of alumina in the final product. A preferred amount of seeds to be added is an amount to yield 0.5 to 8 mole percent of the total final alumina content.

The cesium and/or thallium ions are relatively large cations that become trapped within the aluminosilicate zeolite structure. At least some of them are so trapped in the cages that they are non-exchangeable when using ion exchange techniques. These trapped cesium and/or thallium ions will affect the acidity of the zeolite and because of their positive ion charge and large size, they seem to permit the formation of the zeolite framework with less aluminum in the framework since the presence of less aluminum is clearly measurable. As a result, the zeolite can have higher $SiO_2/Al_2O_3$ ratios with ratios as high as 7 being obtained. The higher the $SiO_2$ content, the greater the steam and thermal stability of the resulting zeolite. Such stability is very advantageous when the zeolite is used as a catalyst, since it can be used at higher temperatures and it can withstand more severe regeneration procedures.

In the preferred practice of our invention, sodium silicate solution is utilized which comprises a solution of sodium silicate having a $Na_2O/SiO_2$ ratio of about 0.30 to 0.35 dissolved in water in amounts which range from about 34 to 40 weight percent solids. Sodium silicates having other $Na_2O/SiO_2$ ratios can be used, but the above ratio is preferred. An aluminum sulfate solution may be used as a source of $Al_2O_3$ and sulfate wherein an aluminum sulfate hydrate having the composition $Al_2(SO_4)_3$ 13–18 $H_2O$ is dissolved in water to produce a solution containing about 4 to 9 percent by weight $Al_2O_3$. Another source of $Na_2O$ and $Al_2O_3$ is sodium aluminate solution which comprises from about 15 to 40 weight percent sodium aluminate, having a composition 1.2 to 1.8 $Na_2O\cdot Al_2O_3$ dissolved in water. These reactant compositions are optimum in the sense that they are available or readily made in a commercial plant.

In the event a sodium aluminate solution is utilized to provide all the alumina present in the final reaction mixture, a mineral acid such as sulfuric acid, hydrochloric acid or nitric acid solution may be added to provide the desired effective free soda and water level in the final reaction mixture indicated above. It is to be noted that the effective soda level is that quantity of soda which is not neutralized by the presence of inorganic acid. In the reaction mixtures indicated above, the quantity of sodium salt, i.e., $Na_2SO_4$, $NaCl$ or $NaNO_3$ is to be considered inactive insofar as the zeolite synthesis is concerned. In other words, the sodium ion indicated as an acid sodium salt is not used to calculate the critical soda to silicate and soda to alumina ratios required to produce the zeolite.

The cesium which is used in making this new zeolite can be obtained from many compound sources. For example, any soluble salt such as cesium carbonate, cesium chloride, cesium sulfate or cesium hydroxide can be used. An additional way to obtain the cesium is to treat a mineral containing cesium with an acid which dissolves the mineral and provides the cesium in the resulting liquid. For example, when the mineral pollucite having the formula $CsNaAl_2Si_4O_{12}$ is used, it can be treated with a strong mineral acid such as hydrochloric acid which leaches out the cesium as a soluble salt. Pollucite is also an advantageous mineral to use since it can provide some of the alumina for the zeolite. In addition to using the cesium salt obtained in the filtrate from the acid treatment of the pollucite mineral, it is also possible to use the entire acid reaction mixture including the pollucite residue when making the zeolite.

The acid treatment of pollucite technique reduces the overall cost since it does not require an expensive cesium salt as the cesium source. This technique also is beneficial since the acid used in the leaching process can also be used to neutralize the excess $Na_2O$ in the reaction mixture instead of having the alum neutralization step.

Cesium can be added to the reaction mixture by at least two different methods. In one method all the cesium will be added in the initial reaction mixture before any seeds are added. In other words, in this embodiment the seeds used are the ones described above and they do not contain any cesium. In the second method all of the cesium required for the final product can be added from seeds having the composition identified above but which also contain cesium. In addition any combination of these two methods can be used to add the required cesium to the mixture.

Although most of the discussion so far has been with the use of cesium, it is also contemplated to substitute for the cesium or use in combination with the cesium, thallium having a valence of one. Again, the thallium can be provided in the form of thallium hydroxide or any other salt form suitable for the addition of cesium. Throughout this specification and claims, the equivalent use of these two materials is intended.

The zeolite obtained with this cesium and/or thallium can also be rare earth exchanged to provide superior catalytic properties. When this zeolite is combined with a rare-earth exchanged Y zeolite, the composite catalyst exhibits an increase in high catalytic activity with superior gasoline and coke selective cracking activity.

This new zeolite can also be exchanged with an ammonium solution to increase the hydrogen ion content. Use of this form of the zeolite in combination with a rare-earth exchanged Y will result in a significant increase in the percent conversion and the yield of high octane aromatic products such as benzene, toluene and xylene. In addition these materials show an extraordinary activity for polymerizing olefins to aromatics as shown by the relative decrease in the amount of olefins produced as compared to the amount of aromatic materials obtained on cracking.

In addition to exchanging the CSZ-1 zeolite with rare earths, it can also be substantially exchanged with cations of elements of Groups 2-8 of the Periodic Table to obtain a hydrocarbon conversion catalyst. This catalyst can be used alone or in combination with a faujasite zeolite exchanged with cations of elements of Groups 2-8 of the Periodic Table.

When used in the severe conditions of a hydrocarbon conversion catalyst, it may be used in the above-described forms or may be suitably embedded in an amorphous material such as silica gel, or a cogel of silica and at least one other metal oxide, wherein the metal is selected from Groups II-A, III-A and IV-B of the Periodic Table, e.g. alumina, titania, magnesia, etc. The use of such composite materials may be valuable in fluidized and moving bed operations since they may be readily formed into particles of a desired size. The composites may be formed by incorporating the zeolite crystals into a suitable hydrogel, e.g. silica-alumina hydrogel; subjecting the mixture to high agitation conditions with added water, if necessary, to produce a homogeneous fluid dispersion; and finally spray drying the resulting mixture.

This zeolite can also be used for its sorptive properties. For example, it has a capacity to adsorb normal butane, isobutane and water. Once it is known that this new material has sorbent properties, it is possible to exchange the zeolite with conventional ion-exchanging cations to modify the effective size of the pore openings. The zeolite can be exchanged with cations of elements of Groups 1-8 of the Periodic Table.

Cesium or thallium are the only two metals having a valence of one that can be used. Although rubidium has a valence of one and there have been suggestions in prior art that rubidium can be used in conjunction with cesium, our research has shown that in making the present superior zeolites, rubidium is not suitable in conjunction with sodium for the crystallization of this new zeolite.

One of the preferred embodiments involves the addition of sufficient seeds to provide 6 percent of the total molar alumina in the final product. This relatively large amount of seeds causes rapid zeolite formation and it conforms to conventional manufacturing operations where it is desired to have an excess amount of seeds present so the seed concentration will be adequate throughout the large reactant batch even if complete mixing does not take place. With these excess seeds, however, is the presence of an excess amount of caustic which must be neutralized by some means such as by alum neutralization. If one wishes to reduce the amount of alum neutralization that is necessary, it has been found possible to produce the present zeolites by using a smaller amount of additional seeds. As one lowers the seeding level homogenization becomes more critical to insure an even distribution of growth centers. Without the proper nucleation sites a competitive impurity (chabazite) may form.

It is also possible to avoid the alum neutralization situation by using metakaolin ($Al_2O_3.2\ SiO_2$). This metakaolin supplies silica without any $Na_2O$. Another technique that can be used is a mixture of aluminate and metakaolin, where the metakaolin is used in sufficient quantity to eliminate the need for $Na_2O$ neutralization by alum or acid.

If faster crystallization rates are desired, then the CSZ-1 can be synthesized from higher stoichiometry compositions. Such compositions, however, have higher chemical input requirements. For example the reaction rate can be increased about 30 percent by increasing the input ratio of $SiO_2/Al_2O_3$ to 16 from a conventional value of 10. This increase in $SiO_2$, however, will approximately double the input reactants.

EXAMPLE 1—Seed Preparation

This example demonstrates the preparation of the seed slurry necessary to promote crystallization of CSZ-1. A solution of sodium silicate containing 8.9% $Na_2O$, 28.7% $SiO_2$ and weighing 541 g was mixed with 315 ml $H_2O$ in a blender. A sodium aluminate solution was prepared by dissolving 160 g NaOH and 32.5 g $Al_2O_3.3\ H_2O$ in 300 ml $H_2O$. The sodium aluminate solution was then added to the silicate solution while blending vigorously. The resultant clear solution was allowed to stand overnight, by which time a smooth gel had formed. This gel was then used as the seed slurry in the following examples.

EXAMPLE 2

This example demonstrates the synthesis of zeolite CSZ-1 from a synthetic gel having a composition:

3.0 $Na_2O$:0.2 $Cs_2O$:$Al_2O_3$:10 $SiO_2$:150 $H_2O$ with 6% of the $Al_2O_3$ derived from the $Al_2O_3$ value of the seed slurry. First 3.6 g NaOH and 15.3 g CsOH were dissolved in 70 ml $H_2O$ and heated to boiling. Then 19.0 g $Al_2O_3.3\ H_2O$ was added to this solution and allowed to dissolve. A silicate solution was prepared by combining 439 g commercial sodium silicate (28.7% $SiO_2$) with 100 ml $H_2O$ in a blender. To this was added 86.6 g of seeds as made in Example 1, the aluminate solution and 107 g of a solution containing 47.9% $Al_2(SO_4)_3.16\ H_2O$. Rapid mixing was maintained throughout the addition steps and afterwards, to ensure a homogenous reaction mixture. The resulting gel was placed in a 250 ml Teflon$^{TM}$ bottle and heated in a forced draft oven at 95° C. for 24 hours.

At the end of this time period, the product was removed, filtered and washed with 1 liter hot, deionized water, and dried at 110° C. The dried product was analyzed by x-ray diffraction to be pure CSZ-1 with the characteristic pattern given in Table I.

EXAMPLE 3

The zeolite CSZ-1 can also be prepared using a variety of $SiO_3$ and/or $Al_2O_3$ sources. CSZ-1 was prepared from a 6% seeded formulation of 3.4 $Na_2O$:0.4 $Cs_2O$:$Al_2O_3$:10 $SiO_2$:150 $H_2O$ using metakaolin to supply the remaining 94% of the $Al_2O_3$ and 20% of the $SiO_2$. A solution containing 6.5 g NaOH and 24 g CsOH in 270 ml $H_2O$ was combined with 307 g sodium silicate solution. To this was added 78 g seeds and 43.2 g of metakaolin. The mixture was then heated, with stirring, for 24 hours, after which the product was judged to be 100% crystalline CSZ-1, having the characteristic x-ray diffraction pattern given in Table I. The nitrogen surface area was 660 m$^2$/g. The product chemical analysis was as follows:

|  | Wt. % | mols/mol $Al_2O_3$ |
| --- | --- | --- |
| $Na_2O$ | 6.40 | 0.52 |
| $Cs_2O$ | 17.0 | 0.32 |
| $Al_2O_3$ | 20.09 | 1.00 |

|  | Wt. % | mols/mol $Al_2O_3$ |
|---|---|---|
| $SiO_3$ | 56.69 | 4.29 | the adsorptive properties can be measured by the general method disclosed by G. R. Landolt in *Anal. Chem.*, 43, p. 613 (1971).

Normal butane capacity was 10.7%, and isobutane capacity was 10.3%; both measured at 20° and 25° C. Water capacity of 33% RH and 25° C. was 18.5 wt.%.

EXAMPLE 4

The product of Example 3 was exchanged twice in 10 fold excess with a 10 wt.% solution of mixed rare earth chloride hexahydrates and calcined at 1000° F. for 3 hours. Analysis of the intermediate product gave 10.6% rare earth oxides, 0.98% $Na_2O$ and a surface area of 560 $m^2/g$. Two additional exchanges were given with equal amount $(NH_4)_2SO_4$ in 10% solution to reduce the sodium oxide content to 0.41%. The zeolite was calcined at 1400° F. for 3 hours and had a surface area of 520 $m^2/g$.

A blend of 15% by weight of the promoter described above in a semi-synthetic clay-silica-alumina gel matrix was tested for catalytic activity by the procedure described by F. G. Ciapetta and O. S. Henderson, *Oil and Gas J.*, 1967, Oct. 16th, p. 88. At 900° F., 16 WHSV and 3 C/O, the result was 66 volume percent conversion.

EXAMPLE 5

CSZ-1 was prepared using the following 6% seeded formulation 3.0 $Na_2O$:0.4 $Cs_2O$:$Al_2O_3$:10 $SiO_2$:150 $H_2O$ 24 g CsOH and 0.6 g NaOH were dissolved in 280 ml $H_2O$ and added to 302 g sodium silicate solution. 78 g seed slurry and 45 g metakaolin were then added, and the mixture heated to 100° C. and held for 40 hours at reflux; at this time x-ray analysis showed 100% crystalline CSZ-1.

Chemical analysis of the dried product gave the composition:

|  | Wt. % | mols/mol $Al_2O_3$ |
|---|---|---|
| $Na_2O$ | 6.7 | 0.60 |
| $Cs_2O$ | 15.6 | 0.31 |
| $Al_2O_3$ | 18.24 | 1.00 |
| $SiO_2$ | 9.46 | 5.54 |

The surface area was 500 $m^2/g$ and $H_2O$ capacity at 33% RH and 25° C. was 21.9 wt.%.

EXAMPLE 6

This example demonstrates the use of less expensive $Cs_2CO_3$ to supply $Cs_2O$ in the method of Example 5 (i.e., 3.0 $Na_2O$:0.4 $Cs_2CO_3$:$Al_2O_3$:10 $SiO_2$:150 $H_2O$/6% seeded), except that 26.1 g $Cs_2CO_3$ was substituted for the CsOH, and 9.6 g additional of NaOH was added to supply the $OH^-$ balance.

After 14 hours at reflux the product was 100% CSZ-1 as determined by x-ray analysis (Table I). The surface area was 460 $m^2/g$ and the composition based on chemical analysis was:

|  | Wt. % | mols/mol $Al_2O_3$ |
|---|---|---|
| $Na_2O$ | 6.87 | 0.61 |
| $Cs_2O$ | 19.2 | 0.38 |
| $Al_2O_3$ | 18.22 | 1.00 |
| $SiO_2$ | 55.68 | 5.19 |

$H_2O$ capacity at 33% RH was 19.1%.

EXAMPLE 7

CSZ-1 may also be synthesized using thallium of valence 1 as the modifying cation, in place of cesium. A metakaolin based formulation:

3.6 $Na_2O$:0.4 $Tl_2O$:$Al_2O_3$:10 $SiO_2$:150 $H_2O$/6% seeded was prepared by dissolving 10.2 g NaOH and 38.3 g T10H $H_2O$ in 280 ml $H_2O$ and combining with 302 g sodium silicate solution. 78 g seed slurry and 45 g metakaolin were added and the entire mixture heated to reflux and held, with mild stirring, for 14 hours. At ths time the product was CSZ-1 (Table I) with a surface area of 410 $m^2/g$.

EXAMPLE 8—Comparison Example

This comparison example is made to evaluate the effect of the presence of rubidium since prior literature has utilized rubidium in conjunction with cesium in the synthesis of other zeolites.

A reaction mixture was prepared by the method of Example 7 with the T10H.$H_2O$ replaced by 21.4 g $Rb_2SO_4$ and an additional 5.4 g NaOH to supply the $OH^-$ balance. The oxide ratio obtained is:

3.6 $Na_2O$:0.4 $Rb_2O$:$Al_2O_3$:10 $SiO_2$:150 $H_2O$/6% seeded The only product obtained after 40 hours reflux was zeolite M as identified by R. M. Barrer and J. W. Baynham, *J. Chem. Soc.*, 2882 (1956). This demonstrates that rubidium is not suitable in conjunction with Na for the crystallization of CSZ-1.

EXAMPLE 9

This example demonstrates the addition of cesium to the seed slurry as a means of introducing cesium in the total mixture. 76.9% g NaOH, 300 g CsOH and 15.6 g $Al_2O_3$ 3 $H_2O$ were dissolved in 296 ml $H_2O$. This solution was then added to 260 g sodium silicate solution while stirring vigorously. After standing for one day, a smooth gel formed which was then used to supply 10% of the alumina and all $Cs_2O$ in the following formulation:

3.4 $Na_2O$:0.1$Cs_2O$:$Al_2O_3$:10$SiO_2$:150$H_2O$.

The final gel was heated for 24 hours at 100° C., at which time the product was 100% CSZ-1 as determined by x-ray diffraction (Table I), with a surface area of 500 $m^2/g$.

EXAMPLE 10

This example demonstrates the use of pollucite mineral ore ($CsNaAl_2Si_4O_{12}$) as a source of $Cs_2O$ in the synthesis of CSZ-1 zeolite, whereby the pollucite is leached with a strong mineral acid for a length of time sufficient to partially or completely destroy the crystal structure of the pollucite, thus releasing cesium as a soluble salt. The acid used in the leaching process can also be used to neutralize the excess $Na_2O$ in the reaction mixture. This procedure obviates the need for the alum neutralization step.

A mixture of 41.2 g powdered pollucite and 46 g 11 M hydrochloric acid were heated to 60° C. and allowed to stand at this temperature for a period of 3 hours. At the end of this time, the mixture was cooled, diluted with 137 ml H$_2$O and filtered. The residual filter cake showed that the pollucite had undergone approximately a 50% loss in crystallinity, indicating substantial change induced by the acid leaching process.

A sodium aluminate solution was prepared by dissolving 19.2 g NaOH in 50 ml H$_2$O and then adding 25.0 g Al$_2$O$_3$ H$_2$O. This was added to a rapidly stirred mixture of 406 g sodium silicate solution, 250 ml H$_2$O and 26.0 g seed slurry of Example 1. To this gel was added the filtrate from the previously described leaching step. The final molar composition of the reaction mixture was

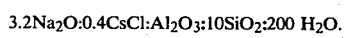
3.2Na$_2$O:0.4CsCl:Al$_2$O$_3$:10SiO$_2$:200 H$_2$O.

The mixture was heated in sealed Teflon containers at a temperature of 75° C. for a period of 24 hours, at which time the sample contained 100% CSZ-1 zeolite.

EXAMPLE 11

A synthesis slurry was prepared using the procedure of Example 10 except for the omission of the filtration step following the acid leaching of the pollucite. Thus the entire solution containing the pollucite residue was used to make an identical molar composition.

After aging for 24 hours at 95° C. the sample was identified as 80% CSZ-1 with 20% pollucite remaining from the leaching step.

EXAMPLE 12—Catalyst Testing Preparation

A large scale batch of CSZ-1 was prepared for catalytic testing. 1200 g CsOH and 160 g NaOH were dissolved in 14.5 liter H$_2$O in a 10 gallon steam-jacketed tank, 15,350 g sodium silicate and 2160 g calcined kaolinite (3 hours at 1300° F.) were added to the hydroxide solution and homogenized. This was followed by the addition of 3900 g seeds from Example 1. The mixture was heated to 100° C. and stirred while crystallizing for 20 hours. The product was filtered and washed twice with 10 gallons hot deionized water (pH=5) and oven dried at 120° C. Analysis of the product was

0.37Cs$_2$O:0.49Na$_2$O:Al$_2$O$_3$:5.6SiO$_2$:6.4H$_2$O, showing a minor amount of H+ exchange from the washing step. The N$_2$ surface area was 540 m$^2$/g and x-ray analysis indicated pure CSZ-1.

EXAMPLE 13

10 g of the product of Example 12 was given two exchanges with 100 g 10% (NH$_4$)$_2$SO$_4$ solution at 100° C. for ½ hour, followed by washing with deionized water. After drying at 100° C. and calcining for 2 hours at 1000° F., this catalyst promoter was blended at 22 wt.% loading with 3% CREY (an ammonium exchanged calcined rare earth exchanged Y zeolite) into a semi-synthetic matrix (60% kaolin clay, 40% high alumina amorphous gel). After steam deactivating at 1250° F. for 8 hours in 5 psig steam, the catalyst was heated for cracking activity in a standard microactivity reactor as described in the Ciapetta et al article, supra, at 900° F., 16 WHSV and 3 C/O. The product distribution for this catalyst, when compared with that for an equilibrium commercial catalyst (CBZ-1), shows high yields of C$_4$ olefins and iso-C$_4$ products, in addition to good gasoline selectivity as shown in Table II below.

EXAMPLE 13A 10 g of the product of Example 12 was exchanged twice with 100 g of a rare-earth chloride solution containing 50 g (La, Ce) Cl$_3$ 6 H$_2$O. The exchanged sample was calcined at 1000° F. for 2 hours. This promoter, containing 0.10% Na$_2$O, was blended into a catalyst at a 22 wt.% level with 3 wt.% rear-earth exchange Y and 75 wt.% of a semi-synthetic matrix, deactivated for 8 hours at 1250° F. in 5 psig steam atmosphere, and tested in a microactivity test reactor described in the Ciapetta et al article, supra, at 900° F., 16 WHSV, and 3 C/O. The data given in Table II show that rare-earth exchanged CSZ-1 is a high activity, gasoline and coke selective cracking catalyst promoter.

TABLE II

| Activity of 22% CSZ-1 Co-Promoted Catalysts | | | |
|---|---|---|---|
| | CBZ-1 Equi- librium | Ex. 13A 22% RE-CSZ-1 3% CREY | Ex. 13 22% H-CSZ-1 3% CREY |
| CONVERSION, V % FEED | 68.89 | 65.51 | 65.46 |
| CONVERSION, W % FEED | 69.16 | 67.95 | 67.90 |
| H2, W % FEED | 0.031 | 0.038 | 0.046 |
| C1, W % | 0.355 | 0.267 | 0.284 |
| C2=, W % | 0.463 | 0.902 | 0.585 |
| C2, W % | 0.242 | 0.037 | 0.316 |
| TOTAL (C1 + C2), W % | 1.060 | 1.206 | 1.186 |
| C2=/TOTAL C2, W/W | 0.66 | 0.96 | 0.65 |
| H2/TOTAL (C1 + C2), W/W | 0.03 | 0.03 | 0.04 |
| TOTAL C3, W % | 4.07 | 3.81 | 4.58 |
| TOTAL Dry Gas, W % | 5.16 | 5.05 | 5.81 |
| C3=, VOL. % FEED | 5.25 | 5.34 | 6.27 |
| C3, V % | 1.56 | 1.04 | 1.41 |
| TOTAL C3, V % | 6.81 | 6.39 | 7.68 |
| C3=/TOTAL C3, V/V | 0.77 | 0.84 | 0.82 |
| C4=, V % | 2.82 | 2.28 | 4.73 |
| i-C4, V % | 6.30 | 4.08 | 8.09 |
| n-C4, V % | 1.13 | 0.72 | 1.41 |
| TOTAL C4, V % | 10.26 | 7.08 | 14.23 |
| C4=/TOTAL C4, V/V | 0.28 | 0.32 | 0.33 |
| i-C4/TOTAL C4, V/V | 0.61 | 0.58 | 0.57 |
| i-C4/n-C4, V/V | 5.55 | 5.66 | 5.73 |
| C5+ GASO., V % | 60.42 | 61.17 | 54.50 |
| C5+ GASO./CONV, V/V | 0.88 | 0.93 | 0.83 |
| C4+ GASO., V % | 70.68 | 68.25 | 68.73 |
| C4+ GASO./CONV, V/V | 1.03 | 1.04 | 1.05 |
| NET COKE, W % CAT. | 0.96 | 0.80 | 1.05 |
| NET COKE, W % FEED | 2.76 | 2.29 | 3.00 |
| C5+ GASO./COKE, V/W | 21.91 | 26.73 | 18.16 |
| CONV./COKE, V/W | 24.98 | 28.63 | 21.80 |
| EST. H2S, W % FEED | 0.12 | 0.40 | 0.40 |

Microactivity test data at 900° F., 16WHSV and 3C/O.
F. G. Ciapetta and D. S. Henderson, Oil & Gas J. (1967), 10/16/67, p. 88.

EXAMPLE 14

This example demonstrates the synthesis of CSZ-1 from higher stoichiometry compositions which allow faster crystallization at the expense of higher chemical input requirements. 13.9 g NaOH and 7.2 g CsOH were dissolved in 60 ml H$_2$O. To this was added 17.5 g Al$_2$O$_3$.3 H$_2$O, which subsequently dissolved. This aluminate solution was poured slowly into a mixture of 388 g sodium silicate solution in 250 ml H$_2$O. The resulting gel was then mixed thoroughly with 46.4 g seeds from Example 1. The total slurry composition was 6.8 Na$_2$O:0.2 Cs$_2$O$_3$:Al$_2$O$_3$:16 SiO$_2$:280 H$_2$O. This mixture was heated to 95° C. in a closed container in a forced draft oven and held for 18 hours. The product of this time was 100% CSZ-1, as determined by x-ray diffraction (Table I).

EXAMPLE 15

The amount of seeds required for efficient nucleation, and hence the amount of excess caustic which must be balanced through alum neutralization, can be significantly reduced as shown in the following example. 13.7 g Na$_2$O and 13.3 g CsOH were dissolved in 120 ml H$_2$O and heated to boiling. Al$_2$O$_3$.3 H$_2$O in the amount of 23.9 g was added and allowed to dissolve. A solution of 469 g sodium silicate solution, 14.4 g seeds and 100 ml H$_2$O was mixed in a blender, to which the warm aluminate solution was slowly added. This was followed by the addition of 82.2 aluminum sulfate (47.9%) solution to give an input stoichiometry of $$3.0Na_2O:0.2Cs_2O:Al_2O_3:10SiO_2:150H_2O$$

After aging at 95° C. in a sealed vial at 95° C. for 24 hours, the product was filtered and dried. X-ray analysis yielded 100% crystalline CSZ-1.

By comparison with Example 2 it can be seen that by reducing the seed input from 86.6 g to 14.4 g, the alum requirement dropped from 107 g to 82 g, or a savings of 23% while achieving essentially the same product.

EXAMPLE 16

The alum savings obtained by the lower seeding levels of Example 15 can be further enhanced to the point of eliminating alum completely through the use of metakaolin as a source of active alumina and silica, and as a balancing agent by lowering sodium silicate input requirements.

In this manner, a reaction mixture was prepared having the same formulation in terms of molar oxide ratios as Example 15, namely:

$$2.0Na_2O:0.2Cs_2O:Al_2O_3:10SiO_2:150H_2O.$$

The quantities of the reactants are compared with those of Example 15.

|  | Example 15 | Example 16 |
| --- | --- | --- |
| Seeds | 14.4 | 14.4 |
| NaOH | 13.7 | 7.0 |
| CsOH | 13.3 | 13.3 |
| C-31 | 23.9 | 9.5 |
| Sodium Silicate | 469 | 391 |
| H$_2$O | 220 | 340 |
| Alum | 82.2 | — |
| Metakaolin | — | 159 |

The reaction mixture was prepared by dispersing the seed slurry into the silicate, 240 ml H$_2$O and the metakaolin. Finally, the aluminate containing the NaOH, CsOH, C-31 and 100 ml of the H$_2$O, was added to form a smooth gel. After heating at 100° C. for 16 hours the product was pure CSZ-1 with a silica/alumina ratio of 5.6.

EXAMPLE 17

The ammonium form of CSZ-1 was prepared as described in Example 13. This was calcined at 1000° F. for 3 hours, then exchanged in 100 q HCl solution at a pH of 4 for 1 hour. 10 g of this promoter on a dry basis were wet blended with 5 g of a low sodium calcined rare-earth Y promoter (CREY) and 85 g of a matrix comprising 30% kaolin clay and 70% silica-alumina gel (25% alumina, 75% SiO$_2$). After oven drying and calcining at 1000° F., the catalyst was tested in a microactivity unit described in the Ciapetta et al article, supra, at 900° F., 16 WHSV and 3 C/O. The results, compared in Table III, with a catalyst promoted only with CREY zeolite, show significant increases in both activity (% conversion) and yield of high octane aromatic products (mainly benzene, toluene and xylenes).

TABLE III

Activity-Octane Benefits of CSZ-1 Promoted Catalysts

| Example | Catalyst Components | | | Microactivity | | | Aromatics/Olefins |
| --- | --- | --- | --- | --- | --- | --- | --- |
|  | CSZ-1 | Co-Catalyst | Matrix | % Conversion | % C$_6$= | % Aromatics |  |
| 17 | 10% H$^+$ | 5% CREY | 85% | 69.8 | 14.5 | 31.3 | 2.16 |
| 17 (Control) | None | 5% CREY | 95% | 58.3 | 21.1 | 24.0 | 1.14 |
| 17A | 10% H$^+$ | 10% HY | 80% | 73.5 | 12.8 | 35.3 | 2.76 |
| 17A (Control) | None | 10% HY | 90% | 57.0 | 24.6 | 25.7 | 1.04 |

% Aromatics = Benzene + toluene + xylenes + trimethylbenzenes.
% C$_6$ = (4 methyl 1 pentene + 3 methyl 1 pentene + 2 methyl 1 pentene + 1 hexene + 3 hexene + trans 2 hexene + 2 methyl 2 pentene + trans 3 methyl 2 pentene + cis 3 methyl 2 pentene) divided by the total C$_6$.

EXAMPLE 17A

Using the ammonium-acid exchanged CSZ-1 sample of Example 17, 10 wt.% of this promoter was blended with an equal weight of a low sodium Z14-US promoter, mixed with 80 wt.% of a semi-synthetic matrix, and tested in an identical manner to the catalyst of Example 17. This CSZ-1 co-promoted catalyst again shows exceptional selectivity for producing products high in aromatic components, as shown in Table III. In both these examples (17 and 17A) H$^+$ CSZ-1 shows extraordinary activity for polymerizing olefins to aromatics, as shown by the higher aromatic/olefin ratios.

EXAMPLE 18

This example demonstrates the crystallization of a high silica CSZ-1 product from an all synthetic starting composition in terms of molar oxides of:

$$2.2\ Na_2O:0.2\ Cs_2O:Al_2O_3:10\ SiO_2:200\ H_2O$$

5.8 g NaOH was dissolved in 37 ml H$_2$O along with 8.3 g CsOH. After heating to a boil, Al$_2$O$_3$ 3 H$_2$O in the amount of 10.4 g was allowed to cool while a silicate mixture comprising 289 g sodium silicate solution, 18 g seeds and 200 ml water was prepared. The cool aluminate solution was added to the silicate/seeds while agitating vigorously. Finally, 84.7 g alum solution was added to the mixture, resulting in a thick smooth gel. The gel was heated, without stirring, for 96 hours at 98° C., at which time the product was 100% CSZ-1 as determined by x-ray diffraction. The SiO$_2$/Al$_2$O$_3$ ratio of the product was 6.6.

What is claimed is:

1. A synthetic crystalline aluminosilicate zeolite having a formula in terms of mole ratios of oxides as follows:

0.05–0.55 M₂O:0.45 to 0.95 Na₂O:Al₂O₃:3–7 SiO₂:x H₂O where M is cesium or thallium and x is 0 to 10 and having an x-ray powder diffraction pattern substantially as set forth in Table I of the specification.

2. A composite catalyst consisting of a mixture of the synthetic crystalline aluminosilicate zeolite according to claim 1 and a rare earth exchanged Y zeolite.

3. A method for preparing the crystalline aluminosilicate zeolite defined in claim 1 which comprises
(a) preparing a mixture containing sources of cesia and/or thallia, an oxide of sodium, an oxide of silicon, an oxide of aluminum, water and sodium aluminosilicate nucleating seeds, said mixture having a final composition in terms of mole ratios of oxides and metal atoms within the following ranges
M/(M+Na): 0.02–0.3
Na₂O/SiO₂: 0.15–0.60
SiO₂/Al₂O₃: 6–30
H₂O/SiO₂: 8–50
where M is Cs or Tl and said seeds being present in an amount to yield 0.1 to 25 mole percent of the total final alumina content,
(b) mixing the composition of step (a) to obtain a homogeneous reaction mixture which forms a gel, and
(c) heating the resulting gel at a temperature of at least 50° C. until the crystals of said zeolite are formed.

4. The method according to claim 3, wherein the temperature in the heating step is maintained between 50° C. and 160° C.

5. The method according to claim 3, wherein the amount of reactants is controlled to obtain a final composition n the following ranges
Cs/(Cs+Na): 0.02–0.15
Na₂O/SiO₂: 0.15–0.60
SiO₂/Al₂O₃: 6–20
H₂O/SiO₂: 15–30

6. The method according to claim 3, wherein the seeds have a composition in terms of mole ratios of oxides of about 16Na₂O:1–9Al₁O₃: 15SiO₂:250–2000-H₂O.

7. The method according to claim 3, wherein the nucleating seeds provide the cesia or thallia added in step (a).

8. The method according to claim 4, wherein the source of cesium is obtained by acid of the mineral pollucite.

9. The method according to claim 3, wherein the seeds are present in an amount to yield 0.5 to 8 mole percent of the total final alumina content.

10. The method according to claim 3, further comprising adding alum to neutralize excess caustic obtained from the seeds.

11. A hydrocarbon conversion catalyst made by substantially exchanging the product of claim 1 with elements of Groups 2–8 of the Periodic Table.

12. Sorbent compositions comprising the product produced by exchanging the product of claim 1 with cations of elements of Groups 1–8 of the Periodic Table.

13. A synthetic crystalline aluminosilicate zeolite comprising the product produced by ion exchanging the zeolite of claim 1 with an ammonium solution followed by heating so as to increase the hydrogen ion content.

14. The method according to claim 3, wherein at least part of the oxide of silicon and at least part of the oxide of aluminium is provided by metakaolin.

15. The method of making a composite catalyst which comprises conducting the method of claim 3 to make the crystalline aluminosilicate zeolite and adding a rare-earth exchanged Y zeolite to form the composite catalyst.

16. The method of making a high hydrogen ion content zeolite which comprises conducting the method of claim 3 to produce the zeolite and further exchanging the zeolite obtained with an ammonium solution and heating to increase the hydrogen ion content of the zeolite.

17. A composite catalyst comprising
(a) the catalyst of claim 11 combined with
(b) a faujasite zeolite exchanged with cations of elements of Groups 2–8 of the Periodic Table.

18. The composite catalyst of claim 17, wherein the catalyst of part (a) is rare-earth exchanged and the part (b) faujasite is rare-earth exchanged and calcined.

19. The composite catalyst of claim 18, further comprising a binder matrix and wherein the rare-earth exchanged part (a) catalyst is present in about 22% by weight and the rare-earth exchanged and calcined part (b) faujasite is present in about 3% by weight.

20. A composite catalyst comprising:
(a) the hydrogen ion exchanged zeolite of claim 13, combined with
(b) a faujasite zeolite exchanged with cations of elements of Groups 2–8 of the Periodic Table.

21. The composite catalyst of claim 20, wherein the part (b) faujasite is rare-earth exchanged and calcined.

22. The composite catalyst of claim 21, further comprising a binder matrix and wherein the hydrogen ion exchanged zeolite of part (a) is present in about 22% by weight and the rare-earth exchanged and calcined part (b) faujasite is present in about 3% by weight.

23. The composite catalyst of claim 21, further comprising a binder matrix and wherein the hydrogen ion exchanged zeolite of part (a) is present in about 10% by weight and the rare-earth exchanged and calcined part (b) faujasite is present in about 5% by weight.

24. A composite catalyst comprising
(a) the hydrogen ion exchanged zeolite of claim 13 combined with
(b) a hydrogen ion exchanged Y-zeolite.

25. The composite catalyst of claim 24, further comprising a binder matrix and wherein the hydrogen ion exchanged zeolite of part (a) is present in about 10% by weight and the ydrogen ion exchanged Y-zeolite of part (b) is present in about 10% by weight.

* * * * *

UNITED STATES PATENT AND TRADEMARK OFFICE
CERTIFICATE OF CORRECTION

PATENT NO. : 4,309,313
DATED : January 5, 1982
INVENTOR(S) : Michael George Barrett and David Evan William Vaughan It is certified that error appears in the above-identified patent and that said Letters Patent are hereby corrected as shown below:

Claim 6, correct line 3 to read:
oxides of about $16Na_2O:1-9Al_2O_3: 15\ SiO_2:250-2000-$ In Claim 8, correct the claim to read:
8. The method according to claim 3, wherein the source of cesium is obtained by acid treatment of the mineral pollucite.

In Claim 25, line 4, change "ydrogen" to --hydrogen--.

Signed and Sealed this

Thirteenth Day of April 1982

[SEAL]

Attest:

GERALD J. MOSSINGHOFF

Attesting Officer     Commissioner of Patents and Trademarks